United States Patent
Akiba et al.

(10) Patent No.: US 8,524,941 B2
(45) Date of Patent: Sep. 3, 2013

(54) PROCESS FOR PRODUCING MONOMER FOR FLUORINATED RESIST

(75) Inventors: Shinya Akiba, Kawagoe (JP); Ryo Nadano, Kawagoe (JP); Yutaka Katsuhara, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 181 days.

(21) Appl. No.: 13/257,193

(22) PCT Filed: Apr. 26, 2010

(86) PCT No.: PCT/JP2010/057327
§ 371 (c)(1),
(2), (4) Date: Sep. 16, 2011

(87) PCT Pub. No.: WO2010/125990
PCT Pub. Date: Nov. 4, 2010

(65) Prior Publication Data
US 2012/0004444 A1 Jan. 5, 2012

(30) Foreign Application Priority Data

Apr. 27, 2009 (JP) ................. 2009-108480
Apr. 27, 2009 (JP) ................. 2009-108488
Apr. 23, 2010 (JP) ................. 2010-099313

(51) Int. Cl.
*C07C 69/653* (2006.01)
(52) U.S. Cl.
USPC ........................................ 560/219
(58) Field of Classification Search
USPC ........................................ 560/219
See application file for complete search history.

(56) References Cited

U.S. PATENT DOCUMENTS

| 6,784,312 B2 | 8/2004 | Miyazawa et al. |
| 6,858,760 B2 | 2/2005 | Komoriya et al. |
| 2003/0224283 A1* | 12/2003 | Allen et al. ............ 430/270.1 |
| 2005/0215836 A1 | 9/2005 | Komata et al. |

FOREIGN PATENT DOCUMENTS

| JP | 59-21648 A | 2/1984 |
| JP | 5-155795 A | 6/1993 |
| JP | 2003-40840 A | 2/2003 |
| JP | 2004-175740 A | 6/2004 |
| JP | 2004-307447 A | 11/2004 |
| JP | 2005-179348 A | 7/2005 |
| JP | 2005-239710 A | 9/2005 |
| JP | 2007-91634 A | 4/2007 |
| JP | 2009-51805 A | 3/2009 |

OTHER PUBLICATIONS

International Search Report with English translation dated Jun. 1, 2010 (five (5) sheets).
Shin Jikken Kagaku Koza, Synthesis and Reactions of Organic Compounds [II], edited by The Chemical Society of Japan and published by Maruzen Co., Ltd., Dec. 1977, pp. 1017-1021, vol. 14 (four (4) sheets).

* cited by examiner

*Primary Examiner* — Wu-Cheng Winston Shen
*Assistant Examiner* — Karen Cheng
(74) *Attorney, Agent, or Firm* — Crowell & Moring LLP

(57) ABSTRACT

According to the present invention, an α-substituted acrylic ester monomer for a fluorinated resist is produced by direct addition of an α-substituted acrylic acid to a fluorinated alkene in the presence of a specific acid catalyst having a sulfonyl group. By the use of such a specific acid catalyst, it is possible to achieve industrial-scale production of the α-substituted acrylic ester monomer for the fluorinated resist by carrying out the target addition reaction of the fluorinated alkene and the α-substituted acrylic acid efficiently during the occurrence of side reactions such as isomerization of the alkene, generation of a diol and excessive addition of the α-substituted acrylic acid.

4 Claims, No Drawings

PROCESS FOR PRODUCING MONOMER FOR FLUORINATED RESIST

TECHNICAL FIELD

The present invention relates to a process for producing an α-substituted acrylic ester monomer of the formula [3] for a fluorinated resist, which is a useful compound as a monomer adaptable to a next-generation ArF laser photoresist.

[Chem. 1]

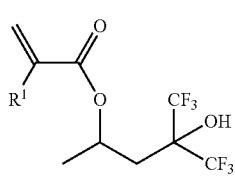

[3]

In the above formula, $R^1$ represents a hydrogen atom, a fluorine atom or a $C_1$-$C_6$ straight or branched alkyl group whose part or all of hydrogen atoms may be substituted with a fluorine atom.

BACKGROUND ART

An α-substituted acrylic ester of the formula [3], which is the target compound of the present invention, is useful as a monomer for a fluorinated resist (see Patent Document 1) and can be produced by general ester synthesis processes. Specific examples of the ester synthesis processes are: (A) reaction of a carboxylic acid halide and an alcohol; (B) reaction of a carboxylic acid anhydride and an alcohol; (C) dehydration condensation of a carboxylic acid and an alcohol; (D) ester interchange of a carboxylic ester and an alcohol. For example, Patent Document 2 discloses a process of reacting a norbornanyl alcohol with an α-substituted acrylic chloride and thereby producing a corresponding norbornanyl ester. Patent Document 3 discloses a process of producing a target ester compound by reaction of an α-substituted acrylic anhydride with an alcohol in the presence of an acid catalyst. It is recited in Patent Document 3 that the reaction proceeds with good selectivity and does not cause precipitation of solid salts so as to allow reduction in solvent amount and improvement in productivity. Non-Patent Document 1 discloses a process of producing a cyclohexyl acrylate by ester interchange of methyl acrylate and cyclohexanol. Further, Patent Documents 4 and 5 each disclose a process of producing a target norbornene ester efficiently by direct addition reaction of an α-substituted acrylic acid to a substituted norbonene.

PRIOR ART DOCUMENTS

Patent Documents

Patent Document 1: Japanese Laid-Open Patent Publication No. 2004-307447
Patent Document 2: Japanese Laid-Open Patent Publication No. 2003-040840
Patent Document 3: Japanese Laid-Open Patent Publication No. 2005-179348
Patent Document 4: Japanese Laid-Open Patent Publication No. 2004-175740
Patent Document 5: Japanese Laid-Open Patent Publication No. 2007-091634

Non-Patent Documents

Non-Patent Document 1: Shin Jikken Kagaku Koza (Vol. 14), Synthesis and Reactions of Organic Compounds [II], P. 1018, edited by The Chemical Society of Japan and published by Maruzen Co., Ltd., December, 1977

SUMMARY OF THE INVENTION

Problems to be Solved by the Invention

There are the following problems in the industrial-scale production of the ester compound of the formula [3]. In the process of Patent Document 2, the α-substituted acrylic chloride is used as the reaction substrate. When the α-substituted acrylic chloride is prepared by chlorination of an α-substituted acrylic acid with thionyl chloride etc., by-products such as an acid anhydride are generated to cause deteriorations in reaction selectivity and yield. Thus, the process of Patent Document 2 is disadvantageous in cost in the case of using expensive α-substituted acrylic acid. In the process of Patent Document 3, an α-substituted acrylic acid is generated as a by-product in an amount of 1 equivalent per 1 equivalent of the target ester compound. The process of Patent Document 3 is thus also disadvantageous in cost in the case of using expensive α-substituted acrylic acid anhydride. Further, it is necessary to remove the α-substituted acrylic acid for commercialization of the ester product. For these reasons, the process of Patent Document 3 is not always an efficient production technique. The present inventors have attempted to produce the target ester compound by dehydration condensation of an α-substituted acrylic acid and an alcohol but could not obtain favorable results due to the occurrence of side reactions caused by large steric hindrance during the progress of the reaction of the α-substituted acrylic acid and the alcohol.

Furthermore, the alcohol is used as the reaction substrate in each of the processes of Patent Documents 1 to 3. In order to apply these processes for the synthesis of the target ester compound of the present invention, it is necessary to convert a fluorinated alkene of the formula [1] (1,1,1-trifluoro-2-(trifluoromethyl)pent-4-ene-2-ol; hereinafter occasionally abbreviated as "BTHB") to a fluorinated diol by a hydroboration technique, an ester addition-ester hydrolysis technique etc., and then, react the fluorinated diol with an acrylic acid, acrylic acid halide, acrylic acid anhydride or acrylic ester as indicated in Scheme 1.

Scheme 1

[Chem. 2]

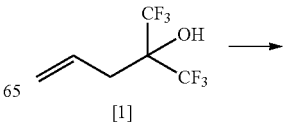

[1]

-continued

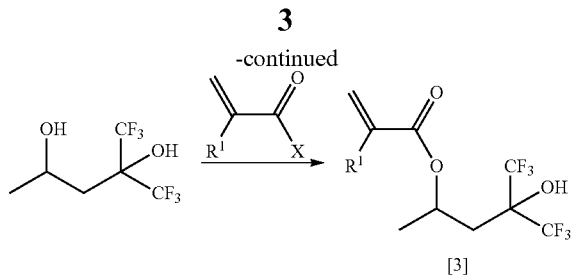

[3]

On the other hand, the present inventors have made researches on the addition of the α-substituted acrylic acid to the fluorinated alkene (BTHB) as in the processes of Patent Documents 4 and 5. This reaction technique is suitable for industrial application because of its less number of process steps and high efficiency of reaction. However, it has been found that: it is likely that a terminal double bond of the fluorinated alkene will be isomerized to an internal double bond under the present conditions (see Scheme 2 and Reference Example 1; and the resulting alkene isomer is low in reactivity and thus difficult to undergo reaction selectively.

Scheme 2

[Chem. 3]

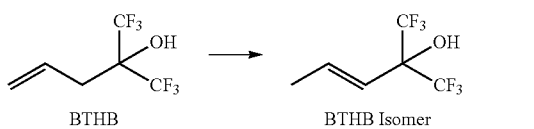

Namely, the isomerization of the fluorinated alkene proceeds competitively with the addition of the α-substituted acrylic acid to the fluorinated alkene. It is thus necessary to carry out the addition of the α-substituted acrylic acid to the fluorinated alkene in consideration of the isomerization of the fluorinated alkene. The present inventors have made researches on the addition of the α-substituted acrylic acid to the fluorinated alkene with the use of various kinds of acid catalysts and found that both of the addition reaction and the isomerization reaction do not proceed with the use of methanesulfonic acid or p-toluenesulfonic acid as the acid catalyst.

Further, it has been shown as a result of further researches that, depending on the reaction conditions, the hydrolysis of the BTHB occurs to generate a fluorinated diol (hereinafter occasionally referred to as "diol" or "iso-BTHB") (see Scheme 3).

Scheme 3

[Chem. 4]

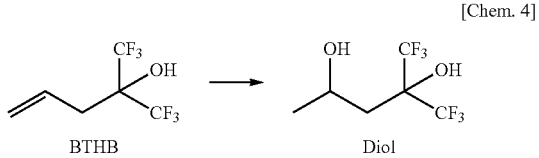

It has also been shown that, with the progress of the reaction time, there takes place excessive addition by which another α-substituted acrylic acid molecule is added to a vinyl moiety of the produced α-substituted acrylic ester (hereinafter this reaction is occasionally referred to as "excessive addition"; and the product of the excessive addition reaction is occasionally referred to as "excessive addition product").

As mentioned above, the processes of Patent Documents 4 and 5 each involves direct reaction of the α-substituted acrylic acid with the fluorinated norbornene in the presence of the acid. There is no need to consider the occurrence of isomerization of the norbornene used as the fluorinated alkene substrate.

It is accordingly an object of the present invention to produce an ester monomer for a fluorinated resist on an industrial scale by carrying out direct addition of an α-substituted acrylic acid to a fluorinated alkene efficiently during the occurrence of side reactions such as isomerization of the fluorinated alkene, generation of a diol and excessive addition of the α-substituted acrylic acid to the target product. None of the prior art documents disclose the conditions to solve all of these problems.

Means for Solving the Problems

In view of the above prior art problems, the present inventors have made extensive researches to develop a production process suitable for industrial-scale production of a monomer for a fluorinated resist. As a result, the present inventors have found that a target monomer for a fluorinated resist can be obtained with favorable yield by reaction of a fluorinated alkene and an α-substituted acrylic acid through the use of a specific acid having a sulfonyl group as an acid catalyst. The present invention is based on the above finding. It is worthy of note that this reaction process allows the target addition reaction to proceed efficiently while preventing the occurrence of side reactions such as isomerization of the fluorinated alkene, generation of a diol and excessive addition of the α-substituted acrylic acid to the target product.

The reaction of the present invention is indicated in Scheme 4.

Scheme 4

[Chem. 5]

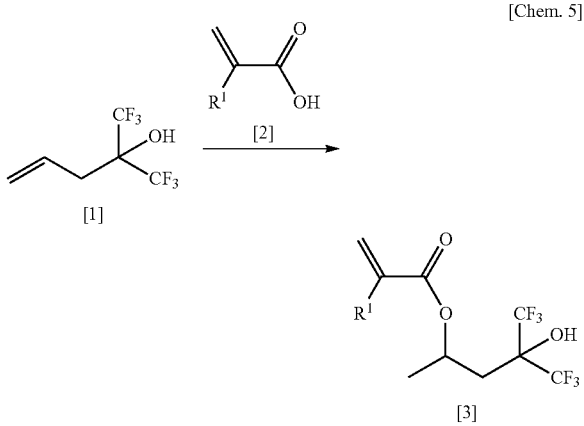

[3]

Namely, the present invention includes the following aspects.

[Inventive Aspect 1]

A process for producing a monomer of the formula [3] for a fluorinated resist by reaction of a fluorinated alkene of the formula [1] with an α-substituted acrylic acid of the formula [2] in the presence of an acid catalyst, wherein the acid catalyst is a sulfonyl-containing acid of the formula [4]:

[Chem. 6]

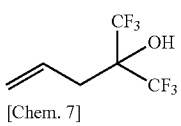

[1]

[Chem. 7]

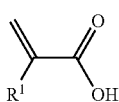

[2]

where $R^1$ represents a hydrogen atom, a fluorine atom or a $C_1$-$C_6$ straight or branched alkyl group whose part or all of hydrogen atoms may be substituted with a fluorine atom

[Chem. 8]

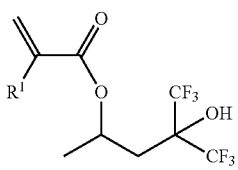

[3]

where $R^1$ has the same meaning as in the formula [2]

[Chem. 9]

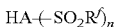

[4]

where A represents an oxygen atom or a carbon atom; $R^f$ may be the same or different and each independently represent a fluorine atom, a hydroxyl group or a $C_1$-$C_6$ fluorinated alkyl group; and n represents an integer of 1 or 3.

[Inventive Aspect 2]

The process for producing the monomer for the fluorinated resist according to Inventive Aspect 1, wherein the acid catalyst has a pKa of −5 or lower.

[Inventive Aspect 3]

The process for producing the monomer for the fluorinated resist according to Inventive Aspect 1 or 2, wherein the reaction is carried out at a temperature of 30 to 200° C.

[Inventive Aspect 4]

The process for producing the monomer for the fluorinated resist according to any one of Inventive Aspects 1 to 3, wherein the fluorinated alkene of the formula [1] is used in an amount of 2 to 10 mol per 1 mol of the α-substituted acrylic acid of the formula [2].

It is possible in the present invention to carry out the target direct addition of the α-substituted acrylic acid to the fluorinated alkene efficiently, for industrial-scale production of the α-substituted acrylic ester monomer for the fluorinated resist, during the occurrence of side reactions such as isomerization of the fluorinated alkene, generation of a diol and excessive addition of the α-substituted acrylic acid to the target product. The target monomer for the fluorinated resist can be produced in one reaction step from the α-substituted acrylic acid efficiently on an industrial scale. In addition, the target addition reaction does not proceed through an acid chloride or acid anhydride. The present production process is thus advantageous in cost particularly in the case of using expensive α-substituted acrylic acid. The resulting monomer for the fluorinated resist is useful as a monomer compound adaptable to a next-generation ArF laser photoresist.

BEST MODES FOR CARRYING OUT THE INVENTION

Hereinafter, the present invention will be described in detail below.

According to the present invention, there is provided a process for producing an α-substituted acrylic ester monomer of the formula [3] for a fluorinated resist, including a step of direct addition of a fluorinated alkene of the formula [1] to an α-substituted acrylic acid of the formula [2] in the presence of a specific acid catalyst.

The following problems arise in the addition reaction of a fluorinated alkene (BTHB) and an α-substituted acrylic acid in the presence of an acid catalyst.

(1) Depending on the kind of the acid catalyst, it becomes likely that a terminal double bond of the fluorinated alkene will be isomerized to an internal double bond. The addition reaction of such an isomer is low in selectivity as the internal double bond is low in reactivity than the terminal double bond.

(2) There is generated a diol by reaction of the BTHB with water in the reaction system, which causes a deterioration in the selectivity of the target product and a load on the operation of separation of the target product from the diol.

(3) With the progress of the reaction time, there is generated an excessive addition product in which another α-substituted acrylic acid molecule is added to a vinyl group of the α-substituted acrylic acid moiety of the target product.

These reactions are summarized in Scheme 5.

Scheme 5

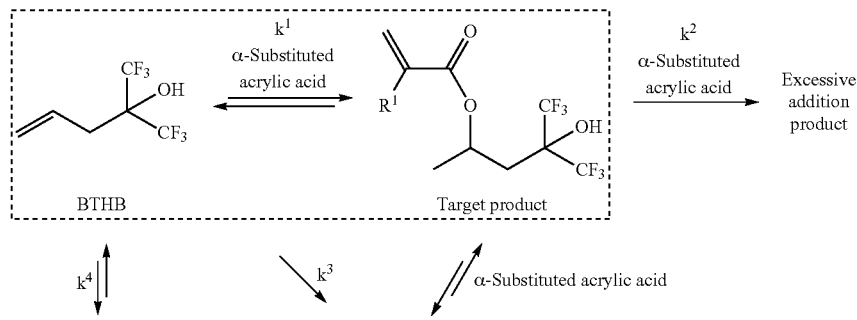

[Chem. 5]

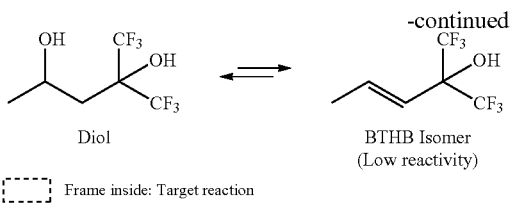

Diol      BTHB Isomer
(Low reactivity)

[----] Frame inside: Target reaction

It is herein defined in Scheme 5 that: $k^1$ is the velocity constant for the addition of the α-substituted acrylic acid to the fluorinated alkene (BTHB); $k^2$ is the velocity constant for the excessive addition of the α-substituted acrylic acid to the target product; $k^3$ is the velocity constant for the isomerization from the BTHB to the BTHB isomer; and $k^4$ is the velocity constant for the generation of the diol by the hydrolysis of the BTHB. It is generally effective to increase the concentration of the α-substituted acrylic acid so as to satisfy the relationship of $k^1>k^3$ or $k^1>k^4$ for the purpose of limiting the isomerization and hydrolysis of the BTHB and thereby forming the target product efficiently. In the present reaction, however, an excessive addition product is also generated. The amount of the excessive addition product unfavorably eventually increases with the concentration of the α-substituted acrylic acid. It is thus effective in the present reaction to select and use the acid catalyst controls so as to satisfy the relationship of $k^1>k^3$ or $k^1>k^4$ under the conditions that the concentration of the α-substituted acrylic acid is low. Although it is theoretically desirable to satisfy the relationship of $k^1>>k^3$ or $k^1>>k^4$ by the action of the acid catalyst, the acid catalyst which catalyzes the addition reaction also catalyzes the side reactions such as isomerization as mentioned above.

The production process of the present invention is characterized in that the acid catalyst and the favorable reaction conditions are set to promote the target addition reaction of the alkene and the acrylic acid efficiently during the occurrence of the isomerization of the alkene, the generation of a diol and the excessive addition of the acrylic acid. It is feasible to perform the production process of the present invention in a batch reaction system. The reaction conditions of the production process will be specifically explained below. It is however understood that various modifications and variations of the reaction conditions will readily occur to those skilled in the art.

The fluorinated alkene of the formula [1] (1,1,1-trifluoro-2-(trifluoromethyl)pent-4-ene-2-ol) used as the raw material in the present invention can be prepared by any known process, for example, by gas-phase contact reaction of hexafluoroacetone and propylene in the presence of activated carbon (see Japanese Laid-Open Patent Publication No. 05-155795).

The α-substituted acrylic acid of the formula [2] used as the raw material in the present invention has, as a substituent $R^1$, a hydrogen atom, a fluorine atom or a $C_1$-$C_6$ straight or branched alkyl group whose part or all of hydrogen atom may be substituted with a fluorine atom. Specific examples of $R^1$ are methyl, ethyl, n-propyl, iso-propyl, n-butyl, iso-butyl, t-butyl, fluorine atom, trifluoromethyl ($CF_3$—), pentafluoroethyl ($C_2F_5$—), $CF_3CH_2$— and $CF_3(CF_3)CH$—. Among others, preferred are those high in acidity in terms of reactivity. Thus, fluorine atom or fluorine-substituted alkyl group is suitably used. Further, hydrogen atom, methyl group or trifluoromethyl group is preferred as $R^1$ in terms of raw material availability and polymerizability with another general-purpose monomer.

The α-substituted acrylic acid can be prepared by any know process. In particular, the α-substituted acrylic acid is readily available as a reagent when $R^1$ is hydrogen atom, methyl group or trifluoromethyl group. It is also known that, when $R^1$ is trifluoromethyl group, the α-substituted acrylic acid can be easily prepared by CO insertion reaction (Heck reaction) of 2-bromo-3,3,3-trifluoropropene with the use of Pd catalyst (see Japanese Laid-Open Patent Publication No. 59-021648).

In the present invention, a sulfonyl-containing acid of the formula [4] is preferably used as the acid catalyst in the addition reaction of the fluorinated alkene of the formula [1] and the α-substituted acrylic acid of the formula [2].

[Chem. 11]

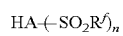

$$HA+SO_2R^f)_n \qquad [4]$$

In the above formula, A represents an oxygen atom or a carbon atom; $R^f$ may be the same as or different from each other and each independently represent a fluorine atom, a hydroxyl group or a $C_1$-$C_6$ fluorinated alkyl group; and n represents an integer of 1 or 3.

The acid of the formula [4] is represented by the formula [5] when A is an oxygen atom and is represented by the formula [6] when A is a carbon atom.

[Chem. 12]

$$HO-SO_2R^f \qquad [5]$$

In the above formula, $R^f$ has the same definition as in the formula [4].

[Chem. 13]

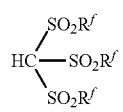

$$[6]$$

In the above formula, $R^f$ has the same definition as in the formula [4].

Examples of the fluorinated alkyl group as $R^f$ are trifluoromethyl ($CF_3$), pentafluoroethyl ($C_2F_5$—), $CF_3CH_2$—, $CF_3(CF_3)CH$—, $C_3F_7$—, $CF_3(CF_2)CH_2$— and nonafluorobutyl ($C_4F_9$—). Preferred are perfluoroalkyl groups such as trifluoromethyl ($CF_3$—), pentafluoroethyl ($C_2F_5$—) and nonafluorobutyl ($C_4F_9$—). In terms of availability, trifluoromethyl ($CF_3$—) is more preferred.

Accordingly, specific examples of the sulfonyl-containing acid of the formula [4] are fluorosulfuric acid, sulfuric acid, trifluoromethanesulfonic acid, nonafluorobutanesulfonic acid and tris(trifluoromethanesulfonyl)methane. In terms of availability, preferred are sulfuric acid, trifluoromethanesulfonic acid and tris(trifluoromethanesulfonyl)methane. Among others, tris(trifluoromethanesulfonyl)methane is particularly preferred.

Preferably, the sulfonyl-containing acid of the formula [4] has a pKa of −5 or lower, more preferably −12 or lower, still more preferably −17 or lower. If the pKa of the sulfonyl-containing acid is higher than −5, the addition reaction unfavorably does not proceed or proceeds at a very slow rate. There is no particular limitation on the lower limit of the pKa of the sulfonyl-containing acid as long as the addition reaction proceeds in the presence of such an acid catalyst. The pKa of the sulfonyl-containing acid can be set to a level where the sulfonyl-containing acid can be prepared and handled without problems.

The amount of the acid catalyst used in the present reaction cannot be uniquely defined as the effect of the acid catalyst varies depending on the combination of the fluorinated alkene, the α-substituted acrylic acid, the solvent and the acid. The amount of the acid catalyst is generally 0.0001 to 1 mol, preferably 0.005 to 0.5 mol, more preferably 0.01 to 0.2 mol, per 1 mole of the α-substituted acrylic acid substrate. If the amount of the acid catalyst is less than 0.0001 mol per 1 mol of the α-substituted acrylic acid substrate, the effect of the addition of the acid catalyst cannot be obtained unfavorably. It is economically unfavorable if the amount of the acid catalyst exceeds 1 mol per 1 mol of the α-substituted acrylic acid substrate.

The mixing ratio of the α-substituted acrylic acid and the fluorinated alkene is in the range that the amount of the fluorinated alkene is 2 to 10 mol, preferably 3 to 6 mol, more preferably 3.5 to 5 mol, per 1 mol of the α-substituted acrylic acid. If the amount of the fluorinated alkene is less than 1 mol per 1 mol of the α-substituted acrylic acid, both of the selectivity of the reaction and the yield of the target product are deteriorated due to the occurrence of isomerization of the fluorinated alkene. Further, the generation of excessive addition product becomes promoted as the amount of the α-substituted acrylic acid relatively increases. On the other hand, it is economically useless if the amount of the fluorinated alkene is less than 10 mol per 1 mol of the α-substituted acrylic acid.

It is feasible to carry out the present reaction in the coexistence of a solvent although the reaction can proceed even in the absence of a solvent. As the solvent, there can suitably be used at least one kind of compound selected from the group consisting of: nitrile solvents such as acetonitrile and benzonitrile; amide solvents such as N,N-dimethylformamide, N,N-dimethylacetamide and N,N-dimethylimidazolidinone; sulfoxide solvents such as dimethyl sulfoxide; ether solvents such as diethyl ether, diisopropyl ether and dibutyl ether; halogenated solvents such as methylene chloride, chloroform and carbon tetrachloride; aromatic hydrocarbon solvents such as benzene, toluene and xylene; and aliphatic hydrocarbon solvents such as pentane, hexane and heptanes. These solvents can be used solely or in combination of two or more thereof.

In the case of using the solvent, the amount of the solvent used is generally 0.01 to 100 g, preferably 1 to 30 g, more preferably 2 to 10 g, per 1 g of the α-substituted acrylic acid. It is economically undesirable in terms of the efficiency of post treatment and recovery operations if the amount of the solvent exceeds 100 g per 1 g of the α-substituted acrylic acid.

In the present reaction, the reaction temperature is in the range of 30 to 200° C., preferably 50 to 150° C., more preferably 80 to 130° C. If the reaction temperature is lower than 30° C., the reaction rate is so low that the reaction cannot be regarded as a practical production technique. If the reaction temperature is higher than 200° C., the α-substituted acrylic acid is unfavorably polymerized.

Furthermore, the present reaction may be carried out in the coexistence of a polymerization inhibitor in order to prevent polymerization of the α-substituted acrylic acid or of the produced monomer for the fluorinated resist. As the polymerization inhibitor, there can suitably be used at least one compound selected from the group consisting of methoquinone, 2,5-di-t-butylhydroquinone, 1,2,4-trihydroxybenzene, 2,5-bistetramethylbutylhydroquinone, Leuco Quinizarine, Nonflex F, Nonflex H, Nonfex DCD, Nonflex MBP, Ozonone 35, phenothiazine, tetramethylthiuram disulfide, 1,1-diphenyl-2-picrylhydrazyl, 1,1-diphenyl-2-picrylhydrazine, Q-1300, Q-1301 and 2-methoxyphenothiazine. These polymerization inhibitors are commercially and readially available.

The amount of the polymerization inhibitor used is 0.00001 to 0.1 mol, preferably 0.00005 to 0.05 mol, more preferably 0.0001 to 0.01 mol, per 1 mole of the α-substituted acrylic acid substrate. If the amount of the polymerization inhibitor exceeds 0.1 mol per 1 mol of the α-substituted acrylic acid substrate, it is economically unfavorable as there is not so large difference in polymerization inhibiting effect. It is difficult to obtain the effect of the use of the polymerization inhibitor if the amount of the polymerization inhibitor is less than 0.00001 mol per 1 mol of the α-substituted acrylic acid substrate.

For the present reaction, the reactor is preferably made with a lining of tetrafluoroethylene resin, chlorotrifluoroethylene resin, vinylidene fluoride resin, PFA resin or glass, or made of glass or stainless steel.

There is no particular limitation on the method for carrying out the present invention. It is a preferred embodiment of the present invention to place, in the reactor capable of withstanding the reaction conditions, the acid as the catalyst, the solvent and the raw materials such as α-substituted acrylic acid and fluorinated alkene, react the resulting solution by heating the reactor from the outside, confirm the completion of the reaction by monitoring the consumption of the raw materials by sampling etc., and then, cool the reaction solution.

The resulting monomer of the formula [3] for the fluorinated resist is purified by any known process. For example, it is feasible to obtain the monomer as a crude organic product by treating the reaction solution with water or aqueous alkali solution, removing the unreacted remaining α-substituted acrylic acid and the acid catalyst by separation, and distillating the excessive remaining fluorinated alkene. There will be no complicated operation problem due to the use of excessive fluorinated alkene as the fluorinated alkene can be easily separated from the monomer for the fluorinated resist by e.g. an evaporator because of a large difference between the boiling point of the fluorinated alkene and the boiling point of the monomer for the fluorinated resist. The monomer for the fluorinated resist is obtained with high purity upon purification of the crude product by column chromatography, distillation etc.

The reaction product, i.e. the monomer of the formula [3] for the fluorinated resist is obtained in the form of a mixture of two isomers of the following formulas [3a] and [3b].

[Chem. 14]

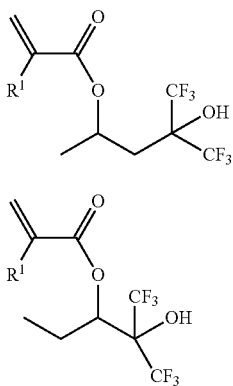

Either one of the isomers can be extracted by any separation process such as column chromatography and used as the resist monomer. Alternatively, the mixture of the isomers can be used as the resist monomer without separation of the isomers.

EXAMPLES

The present invention will be described in more detail below by way of the following examples. Herein, the unit "%" of composition analysis values means "area %" of organic components, other than fluorinated alkene components, each obtained by sampling the reaction mixture, washing the sample sufficiently with water, and then, measuring the resulting organic component by gas chromatography.

Example 1

In a 1-L three-neck flask with a reflux condenser attached to a top portion thereof, 3.5 g (0.0085 mol) of tris(trifluoromethanesulfonyl)methane, 100.0 g (0.7 mol) of α-trifluoromethacrylic acid and 594.3 g (2.8 mol) of 1,1,1-trifluoro-2-(trifluoromethyl)pent-4-ene-2-ol were placed. The flask was then heated in an oil bath of 110° C. After a lapse of 3 hours, the composition of the resulting reaction solution was analyzed by gas chromatography. The total amount (selectivity) of the isomer mixture of a target monomer for a fluorinated resist was 85.1% (the apparent yield of the target monomer was 79.9% as determined by multiplication of the selectivity by the conversion rate of 94.2%). There were also detected, as impurities, 6.0% of α-trifluoromethylacrylic acid raw material and 1.1% of addition product in which one α-trifluoromethylacrylic acid molecule was added to a vinyl group of the acrylic acid moiety of the target product (as excessive addition product). The reaction results (conversion rate, selectivity, yield and by-product detection amounts) are indicated in TABLE 1. The reaction solution was cooled and washed with 200 g of 10% aqueous sodium carbonate (Na$_2$CO$_3$) solution, followed by distillating the fluorinated alkene and collecting a fraction at 80 to 94° C. by distillation under reduced pressure (1.6 Torr=2 kPa). With this, 176 g of the monomer for the fluorinated resist was obtained. The composition of the monomer product was analyzed by gas chromatography. The isomer mixture of the target 5,5,5-trifluoro-4-hydroxy-4-(trifluoromethyl)pent-2-yl 2-(trifluoromethyl)acrylate was obtained with a purity of 98.5%. The amount of the impurities was 1.5%.

Example 2

In a 100-mL three-neck flask with a reflux condenser attached to a top portion thereof, 0.8 g (0.002 mol) of tris(trifluoromethanesulfonyl)methane, 14.0 g (0.1 mol) of α-trifluoromethylacrylic acid and 83.2 g (0.4 mol) of 1,1,1-trifluoro-2-(trifluoromethyl)pent-4-ene-2-ol were placed. The flask was then heated in an oil bath of 110° C. After a lapse of 8 hours, the composition of the resulting reaction solution was analyzed by gas chromatography. The total amount (selectivity) of the isomer mixture of a target monomer for a fluorinated resist was 89.1% (the apparent yield of the target monomer was 83.7% as determined by multiplication of the selectivity by the conversion rate of 93.9%). There were also detected, as impurities, 6.2% of α-trifluoromethylacrylic acid raw material, 0.5% of addition product in which one α-trifluoromethylacrylic acid molecule was added to a vinyl group of the acrylic acid moiety of the target product and 9.5% in total of unidentified impurity substances. The reaction results (conversion rate, selectivity, yield and by-product detection amounts) are indicated in TABLE 1.

Example 3

In a 100-mL three-neck flask with a reflux condenser attached to a top portion thereof, 0.29 g (0.0007 mol) of tris(trifluoromethanesulfonyl)methane, 14.0 g (0.1 mol) of α-trifluoromethylacrylic acid and 41.6 g (0.2 mol) of 1,1,1-trifluoro-2-(trifluoromethyl)pent-4-ene-2-ol were placed. The flask was then heated in an oil bath of 150° C. After a lapse of 9 hours, the composition of the resulting reaction solution was analyzed by gas chromatography. The total amount (selectivity) of the isomer mixture of a target monomer for a fluorinated resist was 84.8% (the apparent yield of the target monomer was 65.5% as determined by multiplication of the selectivity by the conversion rate of 77.3%). There were also detected, as impurities, 22.9% of α-trifluoromethylacrylic acid raw material, 2.2% of addition product in which one α-trifluoromethylacrylic acid molecule was added to a vinyl group of the acrylic acid moiety of the target product and 10% in total of unidentified impurity substances. The reaction results (conversion rate, selectivity, yield and by-product detection amounts) are indicated in TABLE 1.

Example 4

In a 100-mL three-neck flask with a reflux condenser attached to a top portion thereof, 0.86 g (0.002 mol) of tris(trifluoromethanesulfonyl)methane, 8.6 g (0.1 mol) of methylacrylic acid and 83.2 g (0.4 mol) of 1,1,1-trifluoro-2-(trifluoromethyl)pent-4-ene-2-ol were placed. The flask was then heated in an oil bath of 110° C. After a lapse of 7 hours, the composition of the resulting reaction solution was analyzed by gas chromatography. The total amount (selectivity) of the isomer mixture of a target monomer for a fluorinated resist was 89.0% (the apparent yield of the target monomer was 70.3% as determined by multiplication of the selectivity by the conversion rate of 78.9%). There were also detected, as impurities, 21.3% of methacrylic acid raw material, 1.3% of addition product in which one methylacrylic acid molecule was added to a vinyl group of the acrylic acid moiety of the target product and 8.1% in total of unidentified impurity substances. The reaction results (conversion rate, selectivity, yield and by-product detection amounts) are indicated in TABLE 1.

Example 5

In a 100-mL three-neck flask with a reflux condenser attached to a top portion thereof, 0.86 g (0.002 mol) of tris (trifluoromethanesulfonyl)methane, 7.2 g (0.1 mol) of acrylic acid and 83.2 g (0.4 mol) of 1,1,1-trifluoro-2-(trifluoromethyl)pent-4-ene-2-ol were placed. The flask was then heated in an oil bath of 110° C. After a lapse of 10 hours, the composition of the resulting reaction solution was analyzed by gas chromatography. The total amount (selectivity) of the isomer mixture of a target monomer for a fluorinated resist was 55.2% (the apparent yield of the target monomer was 51.5% as determined by multiplication of the selectivity by the conversion rate of 93.3%). There were also detected, as impurities, 6.7% of acrylic acid raw material, 2.1% of addition product in which one acrylic acid molecule was added to a vinyl group of the acrylic acid moiety of the target product and 39.7% in total of unidentified impurity substances. The reaction results (conversion rate, selectivity, yield and by-product detection amounts) are indicated in TABLE 1.

Example 6

In a 1-L three-neck flask with a reflux condenser attached to a top portion thereof, 10.0 g (0.07 mol) of trifluoromethanesulfonic acid, 100.0 g (0.7 mol) of α-trifluoromethylacrylic acid and 594.3 g (2.8 mol) of 1,1,1-trifluoro-2-(trifluoromethyl)pent-4-ene-2-ol were placed. The flask was then heated in an oil bath of 110° C. After a lapse of 6 hours, the composition of the resulting reaction solution was analyzed by gas chromatography. The total amount (selectivity) of the isomer mixture of a target monomer for a fluorinated resist was 80.9% (the apparent yield of the target monomer was 67.2% as determined by multiplication of the selectivity by the conversion rate of 83.1%). There were also detected, as impurities, 17.4% of α-trifluoromethylacrylic acid raw material, 7.7% of addition product in which one α-trifluoromethylacrylic acid molecule was added to a vinyl group of the acrylic acid moiety of the target product (as excessive addition product) and 1.9% iso-BTHB. The mixing ratio of BTHB and BTHB isomer after the reaction was about 1:2. The reaction results (conversion rate, selectivity, yield and by-product detection amounts) are indicated in TABLE 1. The reaction solution was cooled and washed with 200 g of 10% aqueous sodium carbonate ($Na_2CO_3$) solution, followed by distillating the fluorinated alkene and collecting a fraction at 80 to 94° C. by distillation under reduced pressure (1.6 Torr=2 kPa). With this, 120 g of the monomer for the fluorinated resist was obtained. The composition of the monomer product was analyzed by gas chromatography. The isomer mixture of the target 5,5,5-trifluoro-4-hydroxy-4-(trifluoromethyl)pent-2-yl 2-(trifluoromethyl)acrylate was obtained with a purity of 98.5%. The amount of the impurities was 1.5%.

Example 7

In a 1-L three-neck flask with a reflux condenser attached to a top portion thereof, 10.0 g (0.07 mol) of trifluoromethanesulfonic acid, 100.0 g (0.7 mol) of α-trifluoromethylacrylic acid and 297.15 g (1.4 mol) of 1,1,1-trifluoro-2-(trifluoromethyl)pent-4-ene-2-ol were placed. While the flask was heated in an oil bath of 110° C., 297.15 g (1.4 mol) of 1,1,1-trifluoro-2-(trifluoromethyl)pent-4-ene-2-ol was dropped into the flask over 6 hours. After a lapse of 8 hours from the initiation of the dropping, the composition of the resulting reaction solution was analyzed by gas chromatography. The total amount (selectivity) of the isomer mixture of a target monomer for a fluorinated resist was 75.3% (the apparent yield of the target monomer was 61.9% as determined by multiplication of the selectivity by the conversion rate of 82.2%). The reaction results (conversion rate, selectivity, yield and by-product detection amounts) are indicated in TABLE 1.

Example 8

In a 1-L three-neck flask with a reflux condenser attached to a top portion thereof, 10 g (0.07 mol) of trifluoromethanesulfonic acid, 100.0 g (0.7 mol) of α-trifluoromethylacrylic acid and 436.8 g (2.1 mol) of 1,1,1-trifluoro-2-(trifluoromethyl)pent-4-ene-2-ol were placed. The flask was then heated in an oil bath of 110° C. After a lapse of 6 hours, the composition of the resulting reaction solution was analyzed by gas chromatography. The total amount (selectivity) of the isomer mixture of a target monomer for a fluorinated resist was 68.8% (the apparent yield of the target monomer was 55.7% as determined by multiplication of the selectivity by the conversion rate of 81.0%). The reaction results (conversion rate, selectivity, yield and by-product detection amounts) are indicated in TABLE 1.

Example 9

In a 1-L three-neck flask with a reflux condenser attached to a top portion thereof, 9.8 g (0.1 mol) of sulfuric acid, 100.0 g (0.7 mol) of α-trifluoromethylacrylic acid and 594.3 g (2.8 mol) of 1,1,1-trifluoro-2-(trifluoromethyl)pent-4-ene-2-ol were placed. The flask was then heated in an oil bath of 120° C. After a lapse of 7 hours, the composition of the resulting reaction solution was analyzed by gas chromatography. The total amount (selectivity) of the isomer mixture of a target monomer for a fluorinated resist was 65.3% (the apparent yield of the target monomer was 41.2% as determined by multiplication of the selectivity by the conversion rate of 63.1%). The reaction results (conversion rate, selectivity, yield and by-product detection amounts) are indicated in TABLE 1.

Comparative Examples 1 to 5

The same reaction as in Example 1 was performed at a given temperature by placing, in a 100-mL two-neck flask with a reflux condenser attached to a top portion thereof, 10 g of α-substituted acrylic acid and a given mol number of 1,1,1-trifluoro-2-(trifluoromethyl)pent-4-ene-2-ol relative to the α-substituted acrylic acid and using a different kind of acid catalyst (in an amount of 10 wt % relative to the α-substituted acrylic acid). As the acid catalyst, methanesulfonic acid, p-toluenesulfonic acid, camphorsulfonic acid, bis(trifluoroemthanesulfonyl)methane and 1,1,1-trifluoro-N-(trifluoromethanesulfonyl)methanesulfone amide were used in Comparative Examples 1 to 5, respectively. After the completion of the reaction, the composition of the resulting reaction solution was analyzed by gas chromatography. The results are indicated in TABLE 1.

Reference Example

Isomerization of BTHB in the Presence of Acid Catalyst

In a 50-mL three-neck flask with a reflux condenser attached to a top portion thereof, 9.8 g (0.1 mol) of trifluoromethanesulfonic acid as an acid catalyst and 29.7 g (0.14 mol) of 1,1,1-trifluoro-2-(trifluoromethyl)pent-4-ene-2-ol (BTHB) as a fluorinated olefin were placed. The flask was then heated in an oil bath of 100° C. After a lapse of 19 hours, the composition of the resulting reaction solution was analyzed by gas chromatography. The ratio of BTHB and BTHB isomer was 8:92.

TABLE 1

| | α-Substituted acrylic acid | Mol ratio* | Acid catalyst | pKa | BTHB isomerization ratio** |
|---|---|---|---|---|---|
| Example 1 | trifluoromethyl acrylic acid | 1:4 | tris(trifluoromethane sulfonyl)methane | −18 | 1:1 |
| Example 2 | trifluoromethyl acrylic acid | 1:4 | tris(trifluoromethane sulfonyl)methane | −18 | 2.5:1 |
| Example 3 | trifluoromethyl acrylic acid | 1:2 | tris(trifluoromethane sulfonyl)methane | −18 | 1.7:1 |
| Example 4 | methacrylic acid | 1:4 | tris(trifluoromethane sulfonyl)methane | −18 | 13:1 |
| Example 5 | acrylic acid | 1:4 | tris(trifluoromethane sulfonyl)methane | −18 | 24:1 |
| Example 6 | trifluoromethyl acrylic acid | 1:4 | trifluoromethane sulfonic acid | −13 | 1:2 |
| Example 7 | trifluoromethyl acrylic acid | 1:4 | trifluoromethane sulfonic acid | −13 | 2:1 |
| Example 8 | trifluoromethyl acrylic acid | 1:3 | trifluoromethane sulfonic acid | −13 | 1:10 |
| Example 9 | trifluoromethyl acrylic acid | 1:4 | sulfuric acid | −5 | 10:1 |
| Comparative Example 1 | trifluoromethyl acrylic acid | 1:4 | methanesulfonic acid | −2.6 | — |
| Comparative Example 2 | trifluoromethyl acrylic acid | 1:4 | p-toluenesulfonic acid | −2.8 | — |
| Comparative Example 3 | trifluoromethyl acrylic acid | 1:4 | camphorsulfonic acid | about −2 | — |
| Comparative Example 4 | trifluoromethyl acrylic acid | 1:4 | bis(trifluromethane sulfonyl)methane | −1 | — |
| Comparative Example 5 | trifluoromethyl acrylic acid | 1:4 | 1,1,1-trifluoro-N-(trifluoromethanesulfonyl)methanesulfonamide | 1.7 | — |
| Reference Example | — | — | trifluromethane sulfonic acid | −13 | 8:92 |

| | GC composition (%) of by-products | | Conversion rate (%) | Selectivity (%) | Yield (%) |
|---|---|---|---|---|---|
| | Diol | Excessive addition product | | | |
| Example 1 | 1.2 | 1.1 | 94.2 | 85.1 | 79.9 |
| Example 2 | 1.1 | 0.5 | 93.9 | 89.1 | 83.7 |
| Example 3 | 0.9 | 2.2 | 77.3 | 84.8 | 65.5 |
| Example 4 | 1.2 | 1.3 | 78.9 | 89.0 | 70.3 |
| Example 5 | 1.4 | 2.1 | 93.3 | 55.2 | 51.5 |
| Example 6 | 1.9 | 7.7 | 83.1 | 80.9 | 67.2 |
| Example 7 | 1.4 | 5.8 | 82.2 | 75.3 | 61.9 |
| Example 8 | 1.6 | 15.7 | 81.0 | 68.8 | 55.7 |
| Example 9 | 13.8 | 0 | 63.1 | 65.3 | 41.2 |
| Comparative Example 1 | — | — | trace | — | — |
| Comparative Example 2 | — | — | unreacted | — | — |
| Comparative Example 3 | — | — | unreacted | — | — |
| Comparative Example 4 | — | — | unreacted | — | — |
| Comparative Example 5 | — | — | unreacted | — | — |
| Reference Example | 1.3 | — | — | — | — |

*Mol ratio = α-substituted acrylic acid:BTHB
**BTHB isomerization ratio = BTHB:BTHB isomer As is apparent from TABLE 1, it was possible to limit the generation of the iso-BTHB and the excessive addition product and obtain the target product with high yield by the use of the tris(trifluoromethanesulfonyl)methane as the acid catalyst in the reaction system of the trifluoromethylacrylic acid and BTHB (Examples 1 to 3). It was further possible to, even though the BTHB isomer and the excessive addition product were generated, limit the generation of the diol and obtain the target product with relatively high yield by the use of the trifluoromethanesulfonic acid as the acid catalyst in the reaction system of the trifluoromethylacrylic acid and BTHB (Examples 6 to 8). It was possible to, even though the diol was generated, limit the generation of the BTHB isomer and the excessive addition product and obtain the target product by the use of the sulfuric acid as the acid catalyst in the reaction system of the trifluoromethylacrylic acid and BTHB (Example 9). On the other hand, the reaction did not proceed with the use of the high-pH acid as the acid catalyst in the reaction system of the trifluoromethylacrylic acid and BTHB (Comparative Examples 1 to 5).

As described above, the production process of the present invention enables efficient direct addition of the α-substituted acrylic acid to the fluorinated alkene in the presence of a specific acid catalyst having a sulfonyl group even during the occurrence of side reactions such as isomerization of the fluorinated alkene, generation of the diol and excessive addition of the α-substituted acrylic acid to the target product, whereby the α-substituted acrylic ester monomer for the fluorinated resist can be produced on an industrial scale.

Although the present invention has been described with reference to the above specific embodiments, the present invention is not limited to these exemplary embodiments. Various modifications and variations of the embodiments described above can be made without departing from the scope of the present invention.

The invention claimed is:

1. A process for producing a monomer of the formula [3] for a fluorinated resist by reaction of a fluorinated alkene of the formula [1] with an α-substituted acrylic acid of the formula [2] in the presence of an acid catalyst,
   wherein the acid catalyst is a sulfonyl-containing acid of the formula [4]:

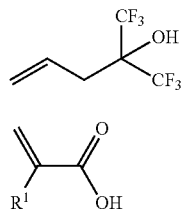

[1]

[2]

where $R^1$ represents a hydrogen atom, a fluorine atom or a $C_1$-$C_6$ straight or branched alkyl group whose part or all of hydrogen atoms may be substituted with a fluorine atom

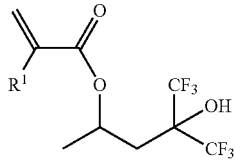

[3]

where $R^1$ has the same meaning as in the formula [2]

$$HA\text{---}(SO_2R^f)_n \qquad [4]$$

where A represents an oxygen atom or a carbon atom; each $R_f$ independently represents a fluorine atom, a hydroxyl group or a $C_1$-$C_6$ fluorinated alkyl group; and n represents an integer of 1 or 3.

2. The process for producing the monomer for the fluorinated resist according to claim 1, wherein the acid catalyst has a pKa of −5 or lower.

3. The process for producing the monomer for the fluorinated resist according to claim 1, wherein the reaction is carried out at a temperature of 30 to 200° C.

4. The process for producing the monomer for the fluorinated resist according to claim 1, wherein the fluorinated alkene of the formula [1] is used in an amount of 2 to 10 mol per 1 mol of the α-substituted acrylic acid of the formula [2].

* * * * *